US010575851B2

(12) United States Patent
Rogers et al.

(10) Patent No.: US 10,575,851 B2
(45) Date of Patent: Mar. 3, 2020

(54) ATRIAL APPENDAGE LIGATION

(71) Applicant: The United States of America, as represented by the Secretary, Department of Health and Human Services, Bethesda, MD (US)

(72) Inventors: Toby Rogers, Washington, DC (US); Kaniska Ratnayaka, Washington, DC (US); Ozgur Kocaturk, Rockville, MD (US); Robert J. Lederman, Chevy Chase, MD (US)

(73) Assignee: The United States of America, as Represented by the the Secretary, Department of Health and Human Services, Bethesda, MD (US)

( * ) Notice: Subject to any disclaimer, the term of this patent is extended or adjusted under 35 U.S.C. 154(b) by 161 days.

(21) Appl. No.: 15/030,574

(22) PCT Filed: Oct. 27, 2014

(86) PCT No.: PCT/US2014/062364
§ 371 (c)(1),
(2) Date: Apr. 19, 2016

(87) PCT Pub. No.: WO2015/061775
PCT Pub. Date: Apr. 30, 2015

(65) Prior Publication Data
US 2016/0249932 A1    Sep. 1, 2016

Related U.S. Application Data (60) Provisional application No. 61/896,048, filed on Oct. 26, 2013.

(51) Int. Cl.
*A61B 17/12* (2006.01)
*A61B 17/04* (2006.01)
(Continued)

(52) U.S. Cl.
CPC .... *A61B 17/12013* (2013.01); *A61B 17/0469* (2013.01); *A61B 2017/00243* (2013.01);
(Continued)

(58) Field of Classification Search
CPC ................................................ A61B 2017/308
See application file for complete search history.

(56) References Cited

U.S. PATENT DOCUMENTS 6,464,629 B1 * 10/2002 Boone ..................... A61B 17/02
600/37
6,676,597 B2 * 1/2004 Guenst ............... A61B 17/0206
600/37
(Continued)

FOREIGN PATENT DOCUMENTS

| WO | WO 01/17437 | 3/2001 |
| WO | WO 2007/131110 | 11/2007 |
| WO | WO 2014/200764 | 12/2014 |

OTHER PUBLICATIONS

Extended European Search Report for related European Application No. 14855406.6, dated May 9, 2017, 7 pages.
(Continued)

*Primary Examiner* — Martin T Ton
(74) *Attorney, Agent, or Firm* — Klarquist Sparkman, LLP (57) ABSTRACT

This disclosure relates to devices and methods for manipulating, such as with a suction based traction device, a target anatomic structure inside the body and delivering an ligation device around the anatomic structure. In particular examples, the target structure can be an atrial appendage, and the devices and methods are for atrial appendage ligation.

18 Claims, 9 Drawing Sheets

(51) Int. Cl.
    *A61B 17/00*     (2006.01)
    *A61B 17/30*     (2006.01)

(52) U.S. Cl.
    CPC ............... *A61B 2017/00867* (2013.01); *A61B 2017/308* (2013.01)

(56) References Cited

U.S. PATENT DOCUMENTS

| | | | |
|---|---|---|---|
| 6,988,984 B2* | 1/2006 | Parsons | A61B 17/02 600/201 |
| 7,976,543 B2 | 7/2011 | Clague et al. | |
| 8,083,664 B2* | 12/2011 | Davis | A61B 17/0218 600/37 |
| 2002/0095067 A1 | 7/2002 | Guenst et al. | |
| 2004/0267303 A1 | 12/2004 | Guenst | |
| 2006/0041194 A1* | 2/2006 | Sorochkin | A61B 17/0218 600/201 |
| 2008/0221593 A1* | 9/2008 | Liddicoat | A61B 17/12009 606/144 |
| 2008/0243183 A1 | 10/2008 | Miller et al. | |
| 2008/0255427 A1 | 10/2008 | Satake et al. | |
| 2010/0069925 A1* | 3/2010 | Friedman | A61B 17/12013 606/144 |
| 2010/0081867 A1 | 4/2010 | Fishler et al. | |
| 2010/0204716 A1 | 8/2010 | Stewart et al. | |
| 2011/0015478 A1 | 1/2011 | Vanden Hoek et al. | |
| 2011/0295060 A1 | 12/2011 | Zenati et al. | |
| 2012/0029271 A1 | 2/2012 | Meyer et al. | |
| 2012/0065662 A1 | 3/2012 | van der Burg et al. | |
| 2012/0065667 A1 | 3/2012 | Javois et al. | |
| 2012/0259314 A1* | 10/2012 | Guo | A61B 17/22 604/509 |
| 2012/0323262 A1 | 12/2012 | Ibrahim et al. | |

OTHER PUBLICATIONS

International Search Report and Written Opinion for International Application No. PCT/US2014/062364, dated Feb. 2, 2015, 10 pages.

International Search Report and Written Opinion for related International Application No. PCT/US2014/040716, dated Sep. 22, 2014, 12 pages.

* cited by examiner

ATRIAL APPENDAGE LIGATION

CROSS-REFERENCE TO RELATED APPLICATIONS

This application is the U.S. National Stage of International Application No. PCT/US2014/062364, filed Oct. 27, 2014, which was published in English under PCT Article 21(2), and which claims the benefit of U.S. Provisional Application No. 61/896,048, filed Oct. 26, 2013, which is incorporated by reference herein in its entirety.

FIELD

This disclosure relates to a device and method for manipulating, such as with a suction based traction device, a target anatomic structure inside the body and delivering a ligation device around the anatomic structure. In particular examples, the target structure can be an atrial appendage, and the devices and methods are for atrial appendage ligation.

BACKGROUND

Stroke is a major cause of mortality and morbidity in the United States. Atrial fibrillation is the commonest cardiac arrhythmia, and it is associated with thrombus formation in the left atrial appendage (LAA). Migration of an atrial thrombus to the brain is a leading cause of stroke. Standard prophylactic treatment is to anti-coagulate a patient with warfarin, but anti-coagulation is often accompanied by side-effects such as bleeding and even hemorrhagic stroke. Alternative interventional devices have been developed to occlude the LAA to avoid thrombus formation. Such devices are deployed either from within the heart (such as the Watchman device or Amplatzer Cardiac Plug) or by ligating the appendage within the pericardium (such as the Lariat or Atriclip procedures). A problem with cardiac occluder devices is the need for trans-septal puncture and anticoagulation to prevent thrombus developing once the device has been deployed. A problem with existing pericardial devices is the necessity of "dry" sub-xiphoid access in the absence of prior pericardial effusions, which predisposes the patient to life-threatening bleeding complications, or the necessity of a major surgical procedure such as a thoracotomy. Another substantial problem of such existing devices is that approaches to isolate the left atrial appendage and establish countertraction to deliver endocavitary occluders or extracavitary occlusion devices or sutures risk rupture or laceration or perforation of the atrial appendage, causes immediate hemodynamic embarrassment and usually requires open surgical repair.

SUMMARY

Some of the exemplary devices disclosed herein include a traction device that is introduced through a delivery catheter in tandem with a delivery device that delivers a ligation device (e.g., a suture, clip, staple, etc.) around or in an anatomic structure in the body, such as the left atrial appendage. In a particular non-limiting embodiment, the traction device is introduced in tandem with a delivery device to grip and manipulate the target tissue to facilitate placement of the ligation device at the target structure. The traction device and delivery device can be introduced coaxially or otherwise through a common delivery catheter, for example together in the single lumen of the delivery catheter, or separately through different lumens of the delivery catheter.

The traction device can include one or more suckers (e.g., suction ports, suction cups, etc.) at a distal end that are coupled to a proximal vacuum source. The traction device is preferably a device for non-traumatically gripping and manipulating the target tissue while the ligation device is deployed.

A particular example of the device is designed to ligate and exclude an atrial appendage from its associated ventricle by puncturing through the contralateral atrial appendage, and thereafter performing the procedure from within the pericardial space. For example, the LAA is excluded from the left atrial cavity, using a procedure performed from within the pericardial space. When ligating the LAA, the pericardial space can be accessed in various manners, such as by puncturing through the tip of the right atrial appendage (RAA) into the pericardium, or by using a transpericardial delivery approach. In such methods, a catheter is advanced into the pericardium, and the traction device and a delivery device are introduced through the catheter into the pericardial space. The LAA is grasped with the traction device while a delivery device deploys the ligation device around the neck or base of the LAA.

In some embodiments, the traction device can grasp a lobe of the LAA using a suction based attachment mechanism. The suction embodiments disclosed herein offer a unique advance in that they redistribute negative pressure along a broader segment of LAA so that traction or countertraction forces are less likely to cause avulsion, injury, or other perforation of the fragile LAA wall. The traction device can exert sufficient traction on the LAA to extend it to define its features and facilitate delivery of a ligation device around it. In other embodiments, the traction is a counter-traction to the force exerted by the delivery device on the target structure.

Some exemplary traction devices comprise two or more independent suckers that attach to surfaces of the LAA or other target structure using suction. In some embodiments, the traction device includes a soft, resiliently deformable pad positioned around each of the suckers. Such pads can provide increased surface area around the sucker for non-traumatically contacting surfaces of the target structure. Each of the suckers can be independently coupled to a vacuum source via independent vacuum tubes that extend through the delivery catheter to a proximal vacuum source. Each sucker can be positioned at a distal end of an independent vacuum tube, and the distal ends of the vacuum tubes can comprise a shape memory material that resiliently regains a predetermined shape when released from a distal end of the delivery catheter. This allows each of the independent vacuum tubes and associated suckers to space apart after deployment from the catheter, and allows them to move and flex independently of each other to better conform to the surface of the target structure and grip it in a non-traumatic manner.

In some embodiments, the traction device includes two articulating distal wings, each including at least one of the suckers. Such traction devices can also include at least one sucker at a junction between the two articulating wings. The wings can be made of a flexible, resilient material, such as silicone rubber that allows the wings to conform around a target structure and place the suckers into contact with surfaces of the target structure in a non-traumatic manner. An articulation angle between the two wings can be adjustable to accommodate different sized target structures. Such adjustability may be achieved by relative axial motion between the delivery catheter and the two wings and/or tubes or rods that are attached to the wings. For example, the articulation angle between the two wings can be adjustable by relative motion between the delivery catheter and a vacuum tube positioned within the delivery catheter that is coupled to a sucker positioned at a junction between the two wings. Such a vacuum tube can be reinforced with a braided layer to assist in pushing and pulling it to cause the articulation of the wings. Each of the two wings can comprise a broad, flexible surface positioned around the suckers located in the wings, such that the flexible surfaces provide increased surface area for non-traumatically contacting surfaces of the target structure.

In some embodiments, at least one of the suckers comprises a suction cup that is resiliently deformable between a compressed configuration that allows it to slide through the delivery catheter, and a deployed configuration in which it expands to form a suction cup.

In some embodiments, the delivery device comprises a pre-shaped, articulated, interrupted, shape-memory loop that carries a suture that is used to ligate the target structure. In some embodiments, the delivery device comprises a semilunar, D-shaped, oval, or circular portion to encircle the target structure. In some embodiments, the delivery device comprises a hollow loop with the suture inside, or a solid loop inside a hollow suture, and the delivery device comprises separable segments that are withdrawn to leave only the suture in place around the target structure.

Exemplary methods of transauricular left atrial appendage ligation are disclosed that utilize the devices disclosed herein to deliver a ligation device to the left atrial appendage, or a neck or base thereof, through an elongated delivery catheter having a lumen, a proximal control end and a distal end. Such methods can comprise: (a) advancing the delivery catheter into the pericardial space from within the right atrial appendage; (b) advancing the traction device from a distal end of the delivery catheter into the pericardial space such that a distal portion of the traction device including the suckers resiliently enlarges to an operative configuration; (c) securing the suckers to the left atrial appendage using suction applied from the proximal control end of the delivery catheter via respective vacuum tubes, and then manipulating the left atrial appendage to facilitate placement of the ligation device on the left atrial appendage, or a neck or base thereof; and/or (d) advancing the delivery device from the distal end of the delivery catheter and positioning the ligation device on the left atrial appendage, or a neck or base thereof.

Disclosed methods can further include detaching the traction device from the left atrial appendage and withdrawing it proximally into the delivery catheter, and withdrawing the delivery device proximally into the delivery catheter while leaving the ligation device on the left atrial appendage, or neck or base thereof.

Some methods also include adjusting a distance between two of the suckers based on an anatomical size of the left atrial appendage prior to securing the suckers to the left atrial appendage The disclosed traction devices can also be used to manipulate other internal anatomic structures. In one example, the disclosed devices can be advanced to the pericardial space via a subxiphoid or transthoracic intrapericardial or intravascular trajectory to the LAA. In some specific non-limiting embodiments, a method is disclosed for accessing a target atrial appendage by introducing a manipulation device through a contralateral atrial appendage into the pericardial space. The manipulation device is then advanced within the pericardial space to the target atrial appendage to manipulate the target. In some embodiments, the manipulation is a ligation of the LAA in a subject who has atrial fibrillation, for example ligation of the LAA at its base or neck to avoid formation of a thrombus within the LAA. In other embodiments the device is applied in an intracavitary fashion to extract an endocavitary cardiac or pulmonary tumor, embolism, thrombus, or embolized devices.

Although the present disclosure specifically describes exemplary devices for occluding the LAA to avoid thrombus formation, the devices disclosed herein can also be used in a variety of different procedures and in combination with a variety of different medical devices to manipulate other tissue within the body, for example by exerting traction or counter-traction on an internal anatomic structure.

The foregoing and other features and advantages of the disclosed technology will become more apparent from the following detailed description of a several embodiments which proceeds with reference to the accompanying figures.

BRIEF DESCRIPTION OF THE FIGURES

FIGS. 15-21 illustrate an exemplary LAA ligation method using the device of FIG. 1.

DETAILED DESCRIPTION

Explanation of Terms

Unless otherwise noted, technical terms are used according to conventional usage. In order to facilitate review of the various embodiments of the disclosure, the following explanation of terms is provided:

A "catheter" is a thin tube typically made of medical grade materials that can be inserted into the body to diagnose or treat disease or perform a medical/surgical procedure. Catheters can be modified to tailor them for cardiovascular, urological, gastrointestinal, neurovascular, ophthalmic and other applications. Catheters can be inserted into any body cavity or lumen, for example over a guide wire or through an introducer sheath. Some catheters may be made of a flexible material and/or have multiple lumens through which different instruments or therapeutic agents can be introduced. The catheter can function independently of or be incorporated into other instruments, such as a flexible endoscope. Endoscopic devices include endoscopes for introduction into the gastrointestinal tract (EGD, enteroscopy, colonoscopy, sigmoidoscopy), respiratory tract (rhinoscopy, bronchoscopy), ear (otoscopy), urinary tract, female reproductive system, abdominal or pelvic cavity (laparoscopy), interior of a joint (arthroscopy), organs of the chest (thoracoscopy and mediastinoscopy), the amnion (amnioscopy), fetus (fetoscopy), epidural space (epiduroscopy), and the eye (as in retinoscopy). The catheter may be inserted separately along with the endoscope, for example by being attached to the endoscope, or be incorporated into the endoscope as a separate lumen within the flexible tube that also contains the endoscope.

The term "comprises" means "includes without limitation." Thus, "comprising A and B" means "including A and B" without excluding additional elements.

"Contralateral" refers to a corresponding part on an opposite side. In anatomy, the terms "ipsilateral" and "contralateral" typically refer to opposing portions of a corporeal lumen having symmetric right and left sides.

A "delivery device" refers to a medical device for delivering a loop, clip, or other object around a target structure within the body. In particular examples, the delivery device comprises a loop for encircling the target structure. In more specific examples, the delivery device comprises a Lariat™ Suture Delivery System from SentreHeart, Inc. In another example, the delivery device comprises an articulated limb assembly as described elsewhere herein.

The terms "distal" and "distally" refer to a location or direction that is, or a portion of a device that when implanted (for example placed within a blood vessel) is further downstream or farther away from the point of insertion. The terms "proximal" and "proximally" refer to a location or direction that is, or a portion of a device that when implanted, or placed within the blood vessel, is further upstream or closest to the point of insertion.

A "flexible member" refers to an element that is sufficiently flexible to be introduced into the body, generally as or through a catheter, and manipulated along a desired path within the body, such as in and around the patient's heart. One example of such a flexible member is a "guide wire" of a conventional catheter. The guide wire also can deliver energy to augment its ability to penetrate tissue, for example by puncturing it, delivering radiofrequency ablative energy or by delivering laser ablative energy.

"Guide wire" refers to a simple guide wire, a stiffened guide wire, or a steerable guide-wire catheter that is capable of puncturing and/or penetrating tissue. The guide-wire also can deliver energy to augment its ability to penetrate tissue, for example by puncturing it, delivering radiofrequency ablative energy or by delivering laser ablative energy. These are examples of a "penetrating device," which is a device capable of penetrating heart tissue, such as the myocardium.

Components of the device disclosed herein can be made of an "MRI-compatible" material. Such materials are safe to use in the body during magnetic resonance imaging of the body, and do not substantially affect imaging quality of the MRI. An "MRI-safe" material is one that does not add substantial risk to a human or equipment by placing it in the magnetic field of an MR environment. Examples of MRI-compatible materials are non-ferrous materials, such as ceramics, plastics and non-magnetic composite materials. Austenitic stainless steels (of the 300 series) are neither ferromagnetic nor paramagnetic and therefore are MRI-compatible. Titanium and aluminum are MRI-compatible, even though they are not ideally paramagnetic. Particularly disclosed MRI-compatible materials of which the protective device may be made include nitinol, MP35N and cobalt-chromium alloys.

The term "protection member" refers to an element that is designed to cooperate with the tensioning element to provide a protected space to a blood vessel or other vital structure along the path of the tensioning element. In general, the protection member is designed so that the blood vessel or vital structure within the protection member experiences less force from the tensioning element than is exerted at adjacent areas at either end of the protection member.

"Suction" is the production of a partial vacuum by the removal of air and/or other fluid in order to remove fluid or secure adherence to surface. Suction is applied by a "sucker" which typically applies negative pressure through an elongated conduit, such as a suction catheter. For example, the suction can be applied through a suction cup or suction port, which is a sucker that distributes the suction force over a target area to distribute the suction forces and avoid tissue injury to a biological target structure. The term "cup" confers no limitation in the specific size or shape of the suction cup. The suction cup can have many different shapes, sizes, and configurations, depending on the target structure to which it is to be applied. In its simplest sense the "cup" is the cylindrical distal end of a suction catheter if the diameter of the end has a sufficient diameter to distribute suction forces over a sufficient area to avoid unacceptable trauma to tissue being adhered to the sucker. Negative fluid pressure is used to adhere the suction cup to a nonporous surface (such as tissue within the body, for example an atrial appendage) and thereby create a partial vacuum within the suction cup. However, the suction cup is generally an enlarged structure on the end of the suction catheter that broadens and/or flattens the area of suction to a greater diameter than the distal tip of the suction catheter. In one example, the working face of the suction cup has a concave or otherwise curved surface; in other embodiments the suction cup can be conical, frustoconical, ovoid, hemispherical, or cylindrical. Yet other shapes of the suction cup can be funnel-shaped, triangular, rectangular, pentagonal, hexagonal, etc. in cross-section. In yet other embodiments the sucker (e.g., suction cup or suction port) is made of a resiliently deformable material that is capable of being compressed to another shape to be delivered through a delivery catheter, but which expands when deployed from the distal tip of the delivery catheter to assume a shape that is capable of applying the suction pressure over an area and maintaining at least a partial seal between the sucker and target tissue to permit the target tissue to be moved by manipulating the sucker.

A "shape memory" material has the ability to return from a deformed shape (temporary shape) to its original (permanent) shape in response to a trigger, such as a physical or thermal trigger, for example release of the material from physical constraint within a catheter lumen. Shape memory materials are typically made of alloys or polymers. In specific examples, the material is a superelastic nickel-titanium alloy sold under the trade name NITINOL or a nickel-chromium alloy such as INCONEL.

As used herein, the term "suture" or "ligature" is meant to encompass any suitable cord-like material and is not limited to only twisted strands, fibers of plastics. A suture is not used in the limited sense of a material that is moved through tissue on a surgical needle to penetrate tissue, but instead more broadly encompasses sutures that are used to encircle and/or compress an organ (as in cerclage of the uterus, ligation of a duct, or mitral or tricuspid annuloplasty of the heart). Both of the terms "suture" and "ligature" include metal and non-metal materials, wire or non-wire materials, natural and synthetic materials, absorbable and non-absorbable that are suitable for ligation or placement of tension or compression on a target structure within the body of a subject. In some embodiments, the suture is a thin and elongated cord. An example of a wire suture or ligature is an annuloplasty wire while examples of non-wire sutures are those made of catgut, silk, polyester, polyglycolic acid, polylactic acid, polydioxanone, nylon, and polypropylene. A variety of suture materials are supplied under names such as ETHILON, MONOCRYL, PROLENE, or VICRYL. Wire sutures are typically made of stainless steel, and can be similar to those used for orthopedic surgery or sternal closure.

The term "ligation device" includes any device for constricting, compressing, and/or closing off an appendage or similar shaped anatomical body. Exemplary ligation devices include a suture (e.g. encircling suture), ligature, clip, clamp, forceps, staple, etc.

"Target structure" includes both biological and non-biological materials. A biological target structure is made of biological tissue, for example an anatomic structure in the body of a subject. Such anatomic structures preferably have a base portion connected to the body and a free portion over and around which the loop can be placed. In the example disclosed herein, the target structure is the atrial appendage, or the neck or base of the atrial appendage. In particular, the target can be the left atrial appendage (LAA), which is a muscular pouch connected to the left atrium of the heart that functions as a decompression chamber during left ventricular systole and during other periods when left atrial pressure is high. The LAA typically has multiple lobes which protrude from the windsock like body; the tail is considered a lobe. A lobe is defined by the following criteria, from Veinot et al., Anatomy of the Normal Left Atrial Appendage, *Circulation* 1997; 96:3112-3115: (1) it was a visible outpouching from the main tubular body of the LAA, usually demarcated by an external crease; (2) it was internally capable of admitting a 2-mm probe (i.e., it was not simply a tag of external adipose tissue); (3) it was occasionally but not necessarily associated with a change in direction of the main tubular body of the LAA; (4) it could lie in a different anatomic plane than the main tubular body: and (5) by definition, the LAA must have at least one lobe (i.e., a tubular body with a blind-ending sac). The target structure can also be the RAA.

"Tensioning material" is any material suitable to place compression on an object (such as an organ) around which it is looped. For example, the tensioning material may be suture that is wrapped around the uterus to perform a B-Lynch procedure to mechanically compress an atonic uterus and stop postpartum hemorrhage, or a left atrial appendage, in which an encircling material is placed under tension to occlude the left atrial appendage and thereby prevent intracavitary thrombus formation which risks thromboembolic stroke.

"Traction" refers to a deliberate pulling of a muscle, organ, or the like, for example to elongate it during a medical or surgical procedure. A "traction device" is a device that can be used to exert traction, such as a transcatheter traction device that can be introduced into the body and attached to a target structure to exert the traction on it.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. The term "comprising A or B" refers to a single element of stated alternative elements or a combination of two or more elements, unless context clearly indicates otherwise. For example, the phrase "rtMRI or echocardiography" refers to real-time MRI (rtMRI), echoradiography, or both rtMRI and echocardiography. Although methods and materials similar or equivalent to those described herein can be used in the practice or testing of the present disclosure, suitable methods and materials are described below. In case of conflict, the present specification, including terms, will control. In addition, the materials, methods, and examples are illustrative only and not intended to be limiting.

Examples from Related Patent Applications

Examples of specific delivery devices are disclosed in U.S. Provisional Application No. 61/834,357, filed Jun. 12, 2013, and entitled "Encircling Suture Delivery System for Flexible Circumferential Suture," and related International Application No. PCT/US2014/040716, filed Jun. 2, 2014, and entitled "Encircling Implant Delivery Systems and Methods," which applications are incorporated by reference herein, and are referred to herein as "the prior applications."

The prior applications disclose exemplary delivery devices for delivering an encircling suture, which are disclosed and described herein as examples of specific delivery devices that can be used in combination with the traction devices disclosed herein. However, the traction devices can be used with other delivery devices, for example the Lariat™ device available from SentreHeart, Inc. In case of any conflict between the incorporated prior applications and the present specification, the present specification will control interpretation.

The delivery device delivers a suture around a target anatomic structure, for example the left atrial appendage. Some of the specific non-limiting embodiments of the delivery device disclosed in the prior applications include two separate hollow limbs that are held together at an articulation by the suture that is to be delivered. The suture extends through the hollow limbs which slide along the suture. At least a distal portion of the limbs is compressible into a delivery shape that allows the limbs to be advanced through the lumen of a delivery catheter. As the distal portions of the limbs move out of the delivery catheter, the limbs cooperatively assume a loop shape that is complementary to the shape of a target around which the encircling suture is to be placed. The two limbs are then separately slid off opposite ends of the suture to leave only the suture in the desired delivery position while maintaining desired (for example constant) suture tension and position on the encircled structure. The delivery device can be used to place encircling sutures around an anatomic structure such as the heart or other organs, and the suture can be tightened to exert compressive force on the anatomic structure.

Devices and methods are also disclosed in the prior applications for delivering an encircling suture around a target structure in the body through a catheter, for example a transcutaneous, transvascular, or intraluminal catheter. Exemplary disclosed devices include separate first and second delivery limbs linked at an articulation by a continuous flexible suture that is to be delivered and which extends through or around the first and second limbs to maintain the first and second delivery limbs together in an articulating relationship at an articulation tip. Each limb may include a proximal limb portion and a distal limb portion, and at least the distal limb portion of each limb is made of a material that is resiliently deformable into the delivery shape. When not deformed into the delivery shape the distal limb portions are configured to cooperatively form with a contralateral limb a loop that can be placed circumferentially around the portion of the target structure.

In some examples disclosed in the prior applications, the target structure is an anatomic or implanted structure in the body of a subject, for instance a target structure having a base portion connected to the body and a free portion over and around which the loop can be passed. In other examples, the target structure is a body organ, a portion of a body organ, or a surgically implanted device. Specific examples of target structures in the prior applications include a heart or atrial appendage, a cecal appendix, a gallbladder, a neoplasm, a uterus, a hemorrhoid, an uvula, an aneurysm, a transected blood vessel or other transected, folded or looped lumen, an intraocular crystalline lens or implanted intraocular lens or lens haptic, a urinary bladder, a kidney, a prostate or a foreign body. Targeted neoplasms particularly include examples such as polyploid or sessile neoplasms, for example colonic or nasal polyps.

In some of the devices disclosed in the prior applications, the distal limb portions of the device are cooperatively biased to assume a loop shape and size substantially complementary to the portion of the target structure around which the loop is to be circumferentially placed. The proximal limb portions of the first and second delivery limbs may be substantially parallel to one another in the delivery shape, and the distal limb portions may be substantially parallel to one another in the delivery shape. For example, the proximal and distal limb portions are constrainable into the delivery shape by a lumen within a flexible delivery catheter though which the encircling suture is to be delivered to the target structure in the body. Delivery catheters typically have a distal end for initial introduction into the body and an open proximal end into which the delivery catheter is introduced and through which it may be controlled. The catheter may optionally have a tip that is capable of perforating tissue, or may be incorporated into or associated with a device (such as an endoscope) that has such capability. The catheter may be rigid or flexible or steerable (for example when incorporated into or otherwise associated with an endoscope).

In some embodiments disclosed in the prior applications, the limbs are flexible to conform to the shape of the lumen within the flexible delivery catheter, for example with the limbs parallel to one another within the confined space within the lumen. The proximal limb portions are able to maintain a substantially parallel relationship when only a distal portion of the proximal limb portions extend from the lumen, and the proximal limb portions may be connected together in at least one location to constrain their relative rotation and/or maintain them substantially parallel.

The suture has first and second terminal ends, and the suture may extend continuously through the delivery limbs within the percutaneous delivery device with the first and second terminal ends of the suture extending from an open proximal tip of the proximal limbs and/or the open proximal end of the delivery catheter. In another embodiment, the terminal ends of the suture emerge through an intermediate opening along each of the first and second delivery limbs (a "monorail" embodiment). The suture may be of any material that is sufficiently flexible and strong, such as fiber or wire, and can perform the intended function of the suture, such as tightening around and securing the target structure. In particular embodiments, the suture is capable of compressing the target structure, for example as a cerclage. The first and second delivery limbs are capable of being withdrawn from the suture, the catheter, and/or the body once the encircling suture is delivered around the target structure thereby leaving only the exposed suture encircling the target structure.

In some embodiments disclosed in the prior applications, the loop is cooperatively formed by the distal limb portions when they are not deformed into the delivery shape, each distal limb portion forming substantially half of the loop, or each distal limb is symmetric or asymmetric with respect to its contralateral limb, or one or both distal limbs is semilunar, semi-ovoid, semi-circular, or substantially C-shaped, J-shaped, L-shaped, S-shaped, V-shaped or U-shaped. In some embodiments, the loop is substantially circular or cordiform and each distal limb portion forms a substantially semi-lunar or semi-cordiform shape joined at the articulation tip. The flexible distal limb portions cooperatively from geometric shapes, and the shape formed by each limb portion may be co-planar or not co-planar with the contralateral limb portion. The loop may extend at a predetermined angle with respect to a longitudinal axis of the proximal limb portion, for example by folding back toward the proximal limb portion.

Methods of use are also disclosed in the prior applications, such as methods of using the device to deliver an encircling suture around a target structure in a body through an elongated delivery catheter having a lumen, a proximal control end and a distal end. The delivery limbs are advanced through the catheter, articulated tip first, with the proximal and distal limb portions conforming to the delivery shape within the delivery catheter with the proximal and distal limb portions substantially conforming to the shape of the lumen of the delivery catheter. As the delivery limbs are further advanced the distal limb portions emerge from the lumen at the distal end of the delivery catheter, and the distal limb portions form the loop while at least a portion of the proximal limb portions are retained within the delivery catheter, for example in a substantially parallel relationship. The loop is then placed around the target structure to encircle it. The first and second delivery limbs may be individually or cooperatively moved to adjust the orientation of the loop with respect to the delivery catheter and the target structure to navigate or deliver the loop around the target. The first and second delivery limbs are then withdrawn over the suture and retracted into the delivery catheter to leave the now-exposed suture positioned and secured around the target structure. The suture can then be tightened around the target structure, for example to compress it. The delivery catheter can then be withdrawn from the suture delivery site or withdrawn entirely from the body.

The methods of the prior applications can include introducing the catheter to the delivery site by a variety of methods. For example, the distal end of the delivery catheter can be introduced percutaneously or intraluminally into the body and the distal end of the delivery catheter then advanced to the target structure within the body. In some embodiments, the delivery catheter is inserted percutaneously through an introducer sheath into the body and advanced intravascularly through the inferior vena cava until the distal end of the delivery catheter penetrates the wall of the heart. The delivery limbs are then advanced out of the distal end of the delivery catheter until the distal delivery limbs form a loop that substantially conforms to the shape of a circumference of the heart. In a particular example disclosed in the prior applications, the loop assumes a preconfigured angle with respect to the proximal portions of the limbs, and the loop is advanced around the apex of the heart within the pericardial space, if the pericardium is intact, until the loop encircles the heart. The delivery limbs are then withdrawn proximally into the catheter to expose the suture which encircles the heart, and the suture is tightened by exerting tension on the terminal ends of the suture, for example to improve the function of a heart valve within the heart.

In some exemplary methods disclosed in the prior applications, the distal end of the delivery catheter penetrates the heart through an atrial appendage, and the loop substantially conforms to a circumference of a targeted atrial appendage of the heart. The loop is advanced around the atrial appendage within the pericardial space, if present, until the loop encircles the targeted atrial appendage. Then the delivery limbs are withdrawn proximally into the catheter to expose the suture encircling the targeted atrial appendage and the suture is tightened by exerting tension on the terminal ends of the suture to exclude the targeted atrial appendage. Alternatively, the distal end of the delivery catheter approaches the heart by a trans-thoracic or sub-xiphoid path and the loop is advanced around the atrial appendage until the loop encircles the atrial appendage. Then the delivery limbs are withdrawn proximally into the catheter to expose the suture which encircles the atrial appendage and the suture is tightened by exerting tension on the terminal ends of the suture to tighten the suture and exclude the atrial appendage.

In alternative embodiments of the methods disclosed in the prior applications, the distal end of the delivery catheter is inserted intraluminally into a body lumen or cavity and advanced to the target structure, for example through or otherwise in association with a laparoscope or bronchoscope. In some embodiments the body lumen is a gastrointestinal, genitourinary, vascular or respiratory lumen. Intraluminal embodiments may be introduced through a body orifice (such as the mouth, nose or anus) instead of transcutaneously. However, a body cavity can also be entered through the skin, for example by insertion of a laparoscope though the abdominal wall into the peritoneum. Examples of other cavities into which the device may be introduced include the peritoneum, an anterior or posterior chamber of the eye, a gastrointestinal cavity, the pelvic cavity, a thoracic cavity, a uterine cavity, a urinary bladder, or a ventricle of the brain.

The devices disclosed in the prior applications can be configured and used to perform a variety of transcatheter procedures such as the cardiovascular procedures discussed above. Other uses include grasping, retrieval, and/or repositioning of foreign bodies such as surgically implanted devices. The device can be used to introduce a protection or compression member to the target structure by advancing the compression member over the suture to a desired position with respect to the target structure. For example, when the target structure is the heart, and the compression device is advanced over the suture to a position on an external wall of the myocardium to exert pressure on its external wall to change a shape and function of a valve of the heart, such as a mitral or tricuspid valve. Alternatively, a protection device is advanced over the suture to a position on an external wall of the myocardium to bridge a coronary artery and avoid compression of the coronary artery when the suture is tightened around the heart. In yet other applications, the target structure is the right ventricular outflow tract or main pulmonary artery.

The foregoing and other features and advantages of the disclosed technology will become more apparent from the following description of additional embodiments, which proceeds with reference to the accompanying figures. The present disclosure provides additional details about trans-auricular atrial appendage ligation, and particularly left atrial appendage ligation, some of which may incorporate or be used with devices and methods generally disclosed in the prior applications, or modifications of those devices and methods.

Exemplary Devices and Procedures

In subjects with atrial fibrillation a thrombus can form in the appendage of the left atrium, or left atrial appendage ("LAA"), and the thrombus can embolize to distant organs. If the embolism travels to the brain, a stroke can occur and result in death or long term disability. Although such patients can be treated with anti-coagulants to help prevent the formation of the thrombus, the use of anti-coagulants can themselves lead to unwanted bleeding, hemorrhagic strokes and death. Surgical methods have been developed to isolate the LAA, for example by suturing or stapling along its base or ostial neck to prevent the flow of blood into the LAA. However, it is desirable to isolate the LAA using minimally invasive or intravascular techniques.

Figure 1:
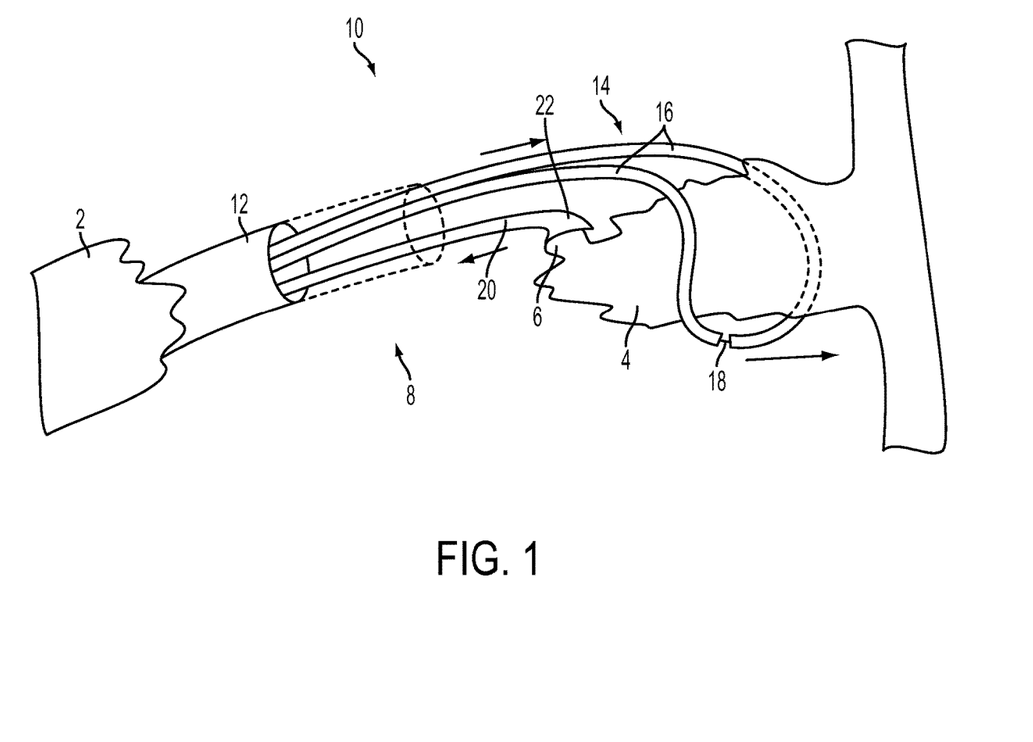
FIG. 1 illustrates a method for exerting traction on the target structure while advancing the suture around the neck of the structure, which in this illustration is the left atrial appendage (LAA). The LAA is grasped on its right side by pulling the grasper to advance the suture around the neck of the LAA.

The delivery devices disclosed herein can be used to deliver a tension suture, tensioning implant, clip, or similar structure, around the base of the LAA. Using a tensioning suture as an example, once the suture is tightened to compress the base of the LAA, blood cannot flow into the lumen of the LAA and formation of a thrombus is avoided. The tension suture can be placed around the LAA using a variety of approaches, for example by introducing a delivery catheter 12 of a transvascular device 10 through the right atrial appendage ("RAA") 2, as is illustrated in FIG. 1. In other methods, a delivery device can be delivered into the pericardial space through the pericardium, such as from a subxiphoid approach. In the example of FIG. 1, the limbs 16 of the suture delivery device 14 are then deployed from the tip of the delivery catheter 12 under fluoroscopic guidance, and the distal portions of the limbs 16 are pre-formed to assume a shape that folds over and loops around the LAA 4. The limbs 16 are then withdrawn through the catheter 12 and the suture 18 tightened to close the neck of the LAA 4 and prevent blood pooling in it.

In particular examples, a catheter 12 is introduced through the RAA 2 into the pericardial space 8 and the limbs 16 of the suture delivery device 14 are deployed within the pericardial space, as illustrated in FIG. 1. A traction device 20 is also introduced through the catheter 12 in tandem with the delivery device 14, such as with the limbs 16 of the delivery device looped around the traction device 20. The suture delivery device 14 and traction device 20 are introduced into the pericardial space 8 and advanced through the pericardial space to the LAA 4. The traction device 20 is designed to non-traumatically attach to the LAA 4, for example to a lobe 6 of the LAA, to exert traction on the LAA to define and elongate the LAA to facilitate placement of the delivery limbs around the LAA.

A "non-traumatic" traction device is one that exerts minimal or no trauma to the atrial appendage during the traction procedure, and does not result in residual long-lasting or permanent dysfunction of the manipulated tissue. In various embodiments, the traction device 20 can comprise a broad-based forceps, snare, or any of the suction based devices disclosed herein, that redistributes traction force onto a large area of tissue to minimize trauma or avulsion or perforation. In the particular example shown in FIG. 1, the traction device 20 includes a suction cup 22 at its distal end for grasping a lobe 6 of the LAA 4.

Figure 2:
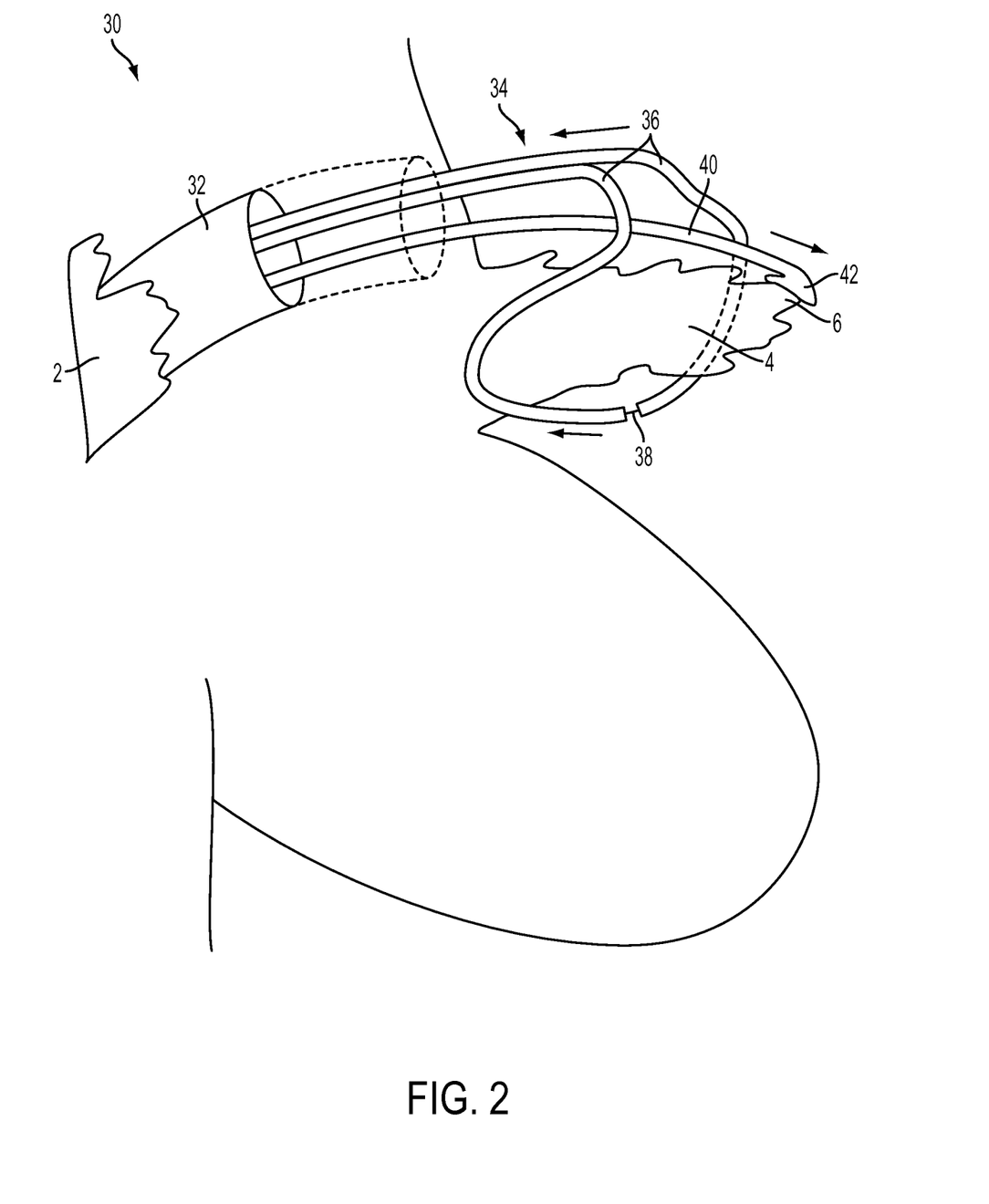
FIG. 2 is similar to FIG. 1, but illustrates an alternative method in which the LAA is grasped on its left side and traction is provided by pushing the grasper as the suture is placed around the LAA neck.

FIG. 2 illustrates an alternative method similar to that shown in FIG. 1, but wherein the LAA 4 is grasped on its left side and traction is provided by pushing the traction device 42 as the suture 38 is placed around the neck of the LAA. In FIG. 2, the device 30 includes a catheter 32 that is introduced through the RAA 2 into the pericardial space 8 and the limbs 36 of the suture delivery device 34 are deployed within the pericardial space. A traction device 40 is also introduced through the catheter 32 in tandem with the suture delivery device 34. The delivery device 34 and traction device 40 are introduced into the pericardial space and advanced through the pericardial space to the LAA 4. The traction device 40 is designed to non-traumatically attach to the LAA 4, for example using a suction cup 42 to grip a lobe 6 of the LAA, to exert traction on the LAA to define and elongate the LAA to facilitate placement of the delivery limbs around the LAA.

Some exemplary traction devices employ one or more distal suction cups, or other suction based grasping features, which can be introduced through a catheter in a compressed configuration, but that are deployable in the pericardial space once the suction feature(s) emerge from the delivery catheter.

Figure 3:
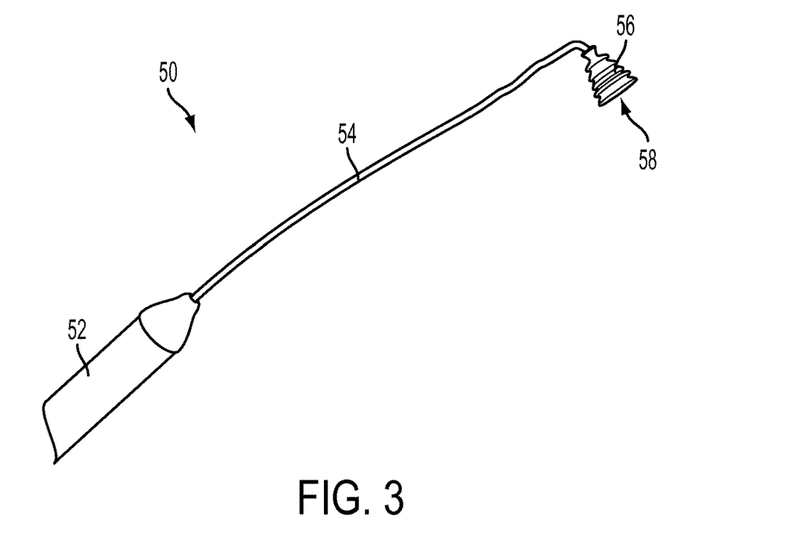
FIGS. 3-5 illustrate an exemplary embodiment of a traction device. The terminal end of a traction catheter contains a funnel-shaped suction cup that is deployable from a flattened configuration (not shown), and the funnel is connected to a source of negative pressure (suction) through the catheter. The suction cup can be non-traumatically attached to the target structure (such as a lobe of the LAA) by suction, and then used to manipulate the target structure to facilitate placement of the suture around the atrial appendage (or its neck or base).
Figure 4:
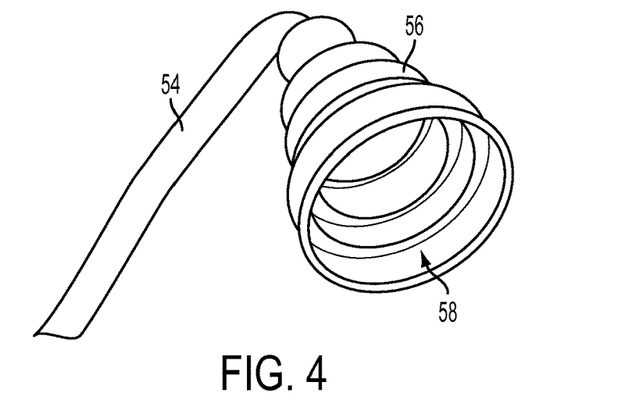
Figure 5:
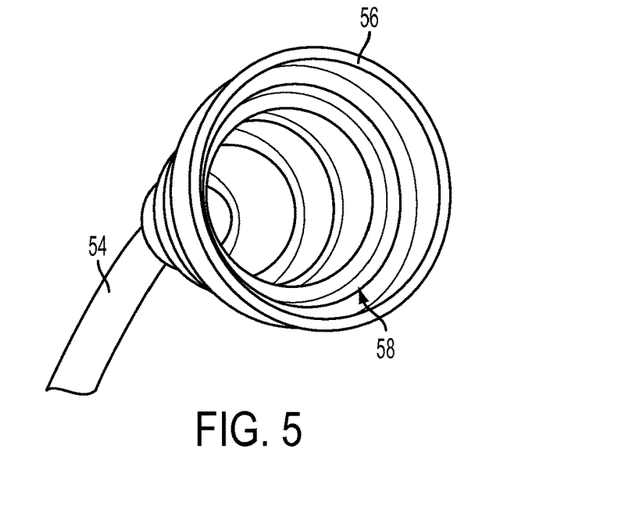

One example of such a traction device 50 is shown in FIGS. 3-5. The traction device 50 includes a tubular vacuum arm 54 with a distal suction cup 56 that has been deployed from the distal tip of the delivery catheter 52, for example within the pericardial space. The suction cup 56 may be made of a memory shape material frame that supports a gas-tight membrane or flexible impermeable polymer material that can be expanded outside the catheter 52 and within the pericardial space. Once expanded, the suction cup 56 can form an opening 58 that can then be attached using suction applied through the vacuum arm 54 to the complex target surface of the LAA, and then effect traction force across a large area and thereby minimize the potential local force maximum which risks injury or avulsion or perforation. Appropriate suction can be applied through the vacuum arm 54 and suction cup 56 to the target structure to maintain a sufficient seal to the target structure and allow movement and traction or countertraction or other manipulation of the target structure. Once the procedure is completed, the suction can be discontinued to release the target structure, and the traction device 50 can be withdrawn through the delivery catheter 52.

A traction device (such as the traction device 50 with the distal suction cup 56) can be introduced through a delivery catheter (such as the catheter 52) in tandem with a suture delivery device. The traction device can be pre-loaded in the delivery catheter with the delivery device encircling it, for example the limbs of the delivery device encircling the suction cup or its suction catheter. The traction device can be attached to the target structure either before or after deployment of the loop around the target structure, and the placement of the loop around the target structure is not impeded by the presence of the traction device which has been delivered with the loop already around the traction device. The traction device can be used to provide traction on the target structure to facilitate placement of the loop around the target structure. In some such embodiments, the traction applied by the traction device is a counter-traction to traction applied by the delivery device. For example, the loop around the LAA may pull or push the LAA in a different direction than the traction applied by the traction device. In some embodiments, the traction and counter-traction are applied in substantially opposite directions. In other embodiments the traction and counter-traction are applied at an angle to one another, for example between 1-179 degrees to one another, such as 15-75, 45-90, or 90 degrees to one another.

Figure 6:
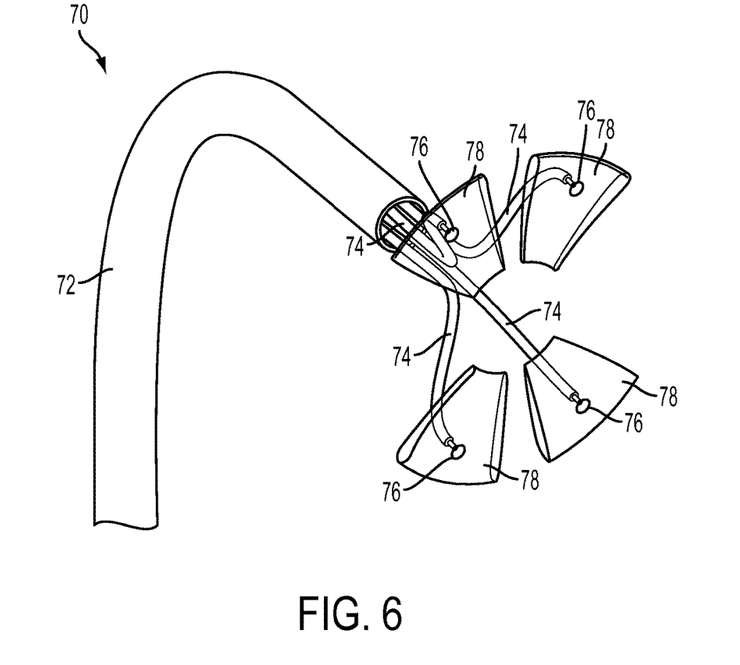
FIGS. 6 and 7 illustrate another exemplary embodiment of a traction device, this embodiment having four discrete suction arms.
Figure 7:
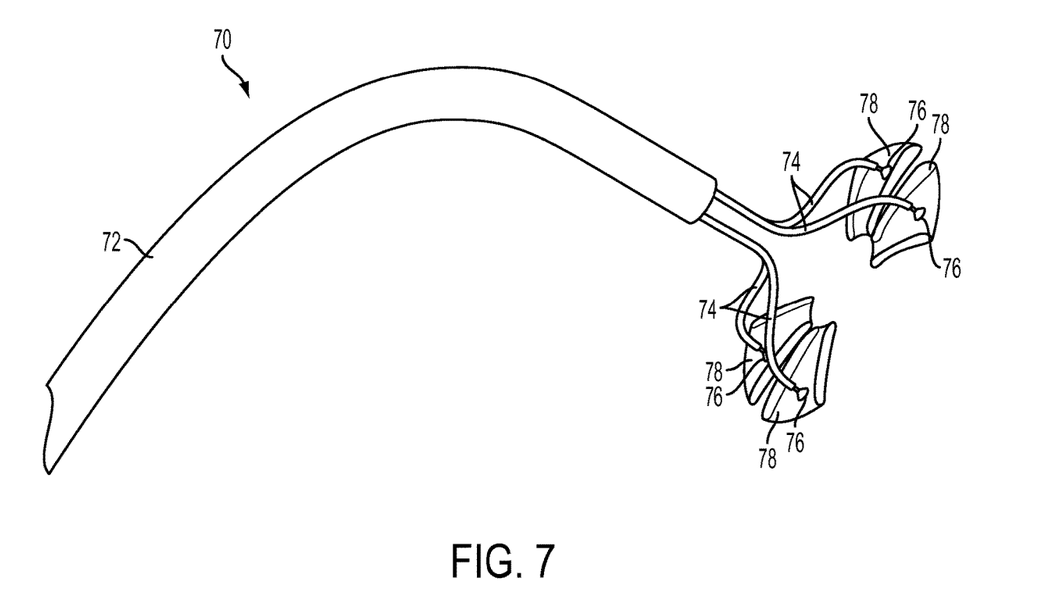
Figure 8:
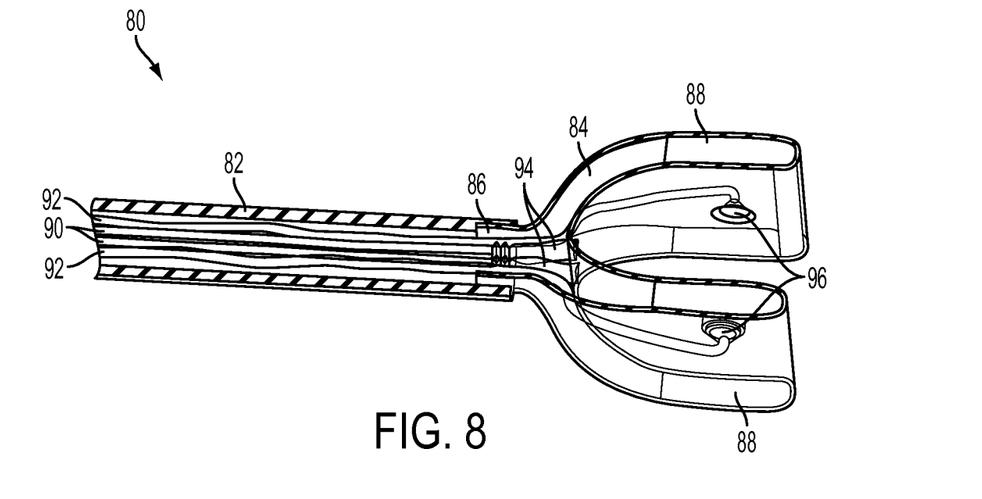
FIGS. 8-14 illustrate yet another exemplary embodiment of a traction device, this embodiment having two opposed suction arms.
Figure 9:
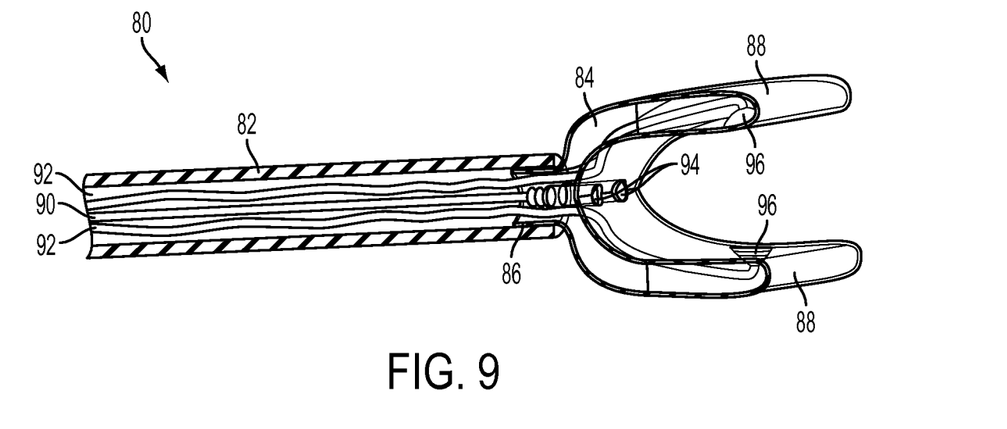
Figure 10:
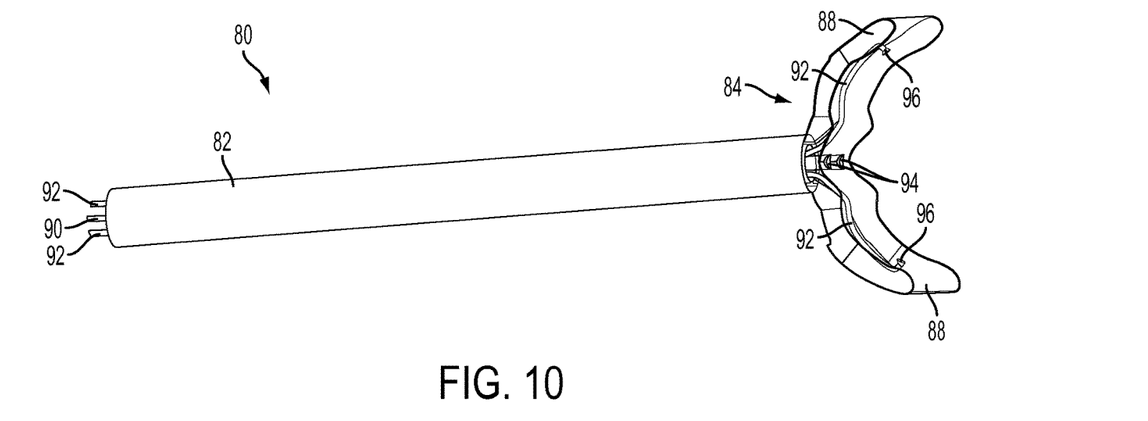

FIGS. 6 and 7 illustrate another exemplary suction based traction device 70, which includes a catheter 72, and a plurality of vacuum tubes 74 terminating in distal suction ports 76 formed in flexible pads 78. In the illustrated example, there are four vacuum tubes 74 each with four respective suction ports 76 (also referred to as abluminal ports) and four respective pads 78, though other numbers vacuum tubes and respective suction ports and pads, such as two, three, five, or more, can be included in alternative embodiments. The use of plural suction ports 76 and associated pads 78 distributes the total suction force over a broader surface area to help minimize trauma to the LAA, and also provides redundancy in case one of the suction ports should fail and detach.

In alternative embodiments, one or more of the suction ports 76 and pads 78 can be replaced with other types of suckers, such as collapsible suction cups, and any such suckers can be made in any desirable size.

The vacuum tubes 74 can comprise nitinol or other shape memory material to allow the vacuum tubes to be deformed to generally linear shape to fit into the catheter 72 and then resiliently return to a preconfigured shape and/or orientation (such as that shown in FIGS. 6 and 7) after deployment from the catheter 72. In some embodiments, the vacuum tubes 74 can comprise shape memory wires embedded into the walls of the vacuum tubes, and in some embodiments the vacuum tubes can also include a braided fabric sheath. In some embodiments, the distal ends of the vacuum tubes 74 can, when freed from the delivery catheter, extend apart from each other to space apart the suction ports 76. In the illustrated embodiment, the tubes 74 curve outwardly away from each other and then curve back to extend generally axially as they connect to the suction ports 76. In other embodiments, the tubes 74 can take various other shapes when freed from the delivery catheter. For example, the tubes can be configured such that the pads 78 face at least partially toward each other with an open region between them, so that the pads can be placed around a target structure, with part of the target structure moving into the central area between the pads, and with the pads being angled to flushly contact the surfaces of the target structure. The tubes 74 can also be flexible enough to readily deform during attachment of the suction ports to the target structure so that the pads and suction ports can readily flex and conform to the target structure for better attachment.

The pads 78 can comprise a resiliently flexible polymeric material, such as silicone rubber, that allows them to readily conform to the shape of the surface of the LAA and provide a non-traumatic attachment. The pads 78 can also comprise one or more marker materials that provide conspicuity during imaging procedures, such as X-ray, MRI, and ultrasound. Exemplary conspicuity materials include iron oxide, stainless steel, barium sulphate iodine, etc.

FIGS. 8-14 illustrate yet another exemplary suction based traction device 80, which includes a catheter 82, a distal gripper 84 comprising two articulating wings 88, and a plurality of vacuum tubes 90, 92 that extend through the catheter 82 and gripper 84 and terminate at respective suction ports 94, 96.

The gripper 84 can comprise a resiliently flexible polymeric material, such as silicone rubber. The gripper can also comprise one or more marker materials that provide conspicuity during imaging procedures, such as X-ray, MRI, and ultrasound. Exemplary conspicuity materials include iron oxide, stainless steel, barium sulphate iodine, etc. The gripper 84 can have a proximal neck 86 that is coupled to the distal end of the catheter 82, such as with the neck 86 secured inside the distal end of the catheter 82 as shown. The two wings 88 of the gripper 84 can articulate, similar to a forceps, along a range of separations, include more open configurations (e.g., FIGS. 10-12) and more closed configurations (e.g., FIGS. 8, 9, 13, and 14) to accommodate different sized anatomic variations of the target structure, such as the LAA. The wings 88 can have a broad, flat shape that provides two large surface areas on each wing that face each other. By virtue of multiple independent suction ports 94, 96, the traction device 80 can be more fault-tolerant and can maintain suction even when there is detachment of one or some of the individual ports. Alternatively, the ports 94, 96 can provided with suction in series for better securement with the LAA.

The vacuum tubes 90 (any number can be included) extend through the catheter 82 and terminate at respective suction ports 94 located at in the gripper at or near the junction of the two wings 88. The ports 94 can have any orientation relative to each other, such aligned side-by-side along the thickness of the gripper 84 and each equidistant between the two wings 88, as illustrated.

The vacuum tubes 92 (any number can be included) each extend through the catheter 82 and extend through one of the wings 88 and terminate at a respective one of the suction ports 96 located on the broad abluminal inner surface of the wings. Each wing 88 can include one or more suction ports 96, and a corresponding number of vacuum tubes 92 can be included in each wing.

Figure 11:
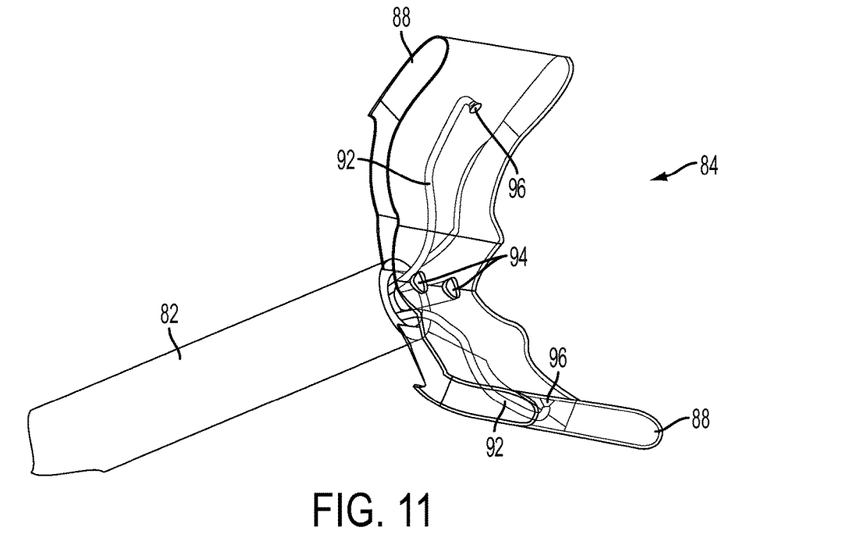
Figure 12:
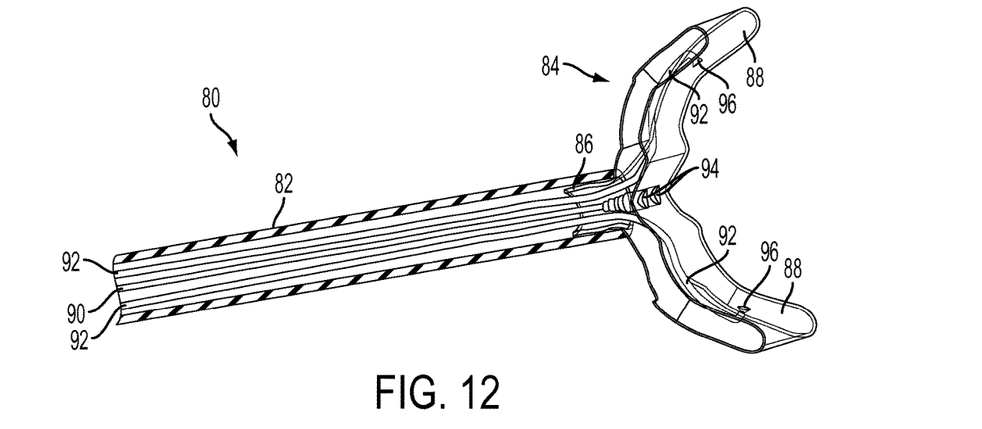
Figure 13:
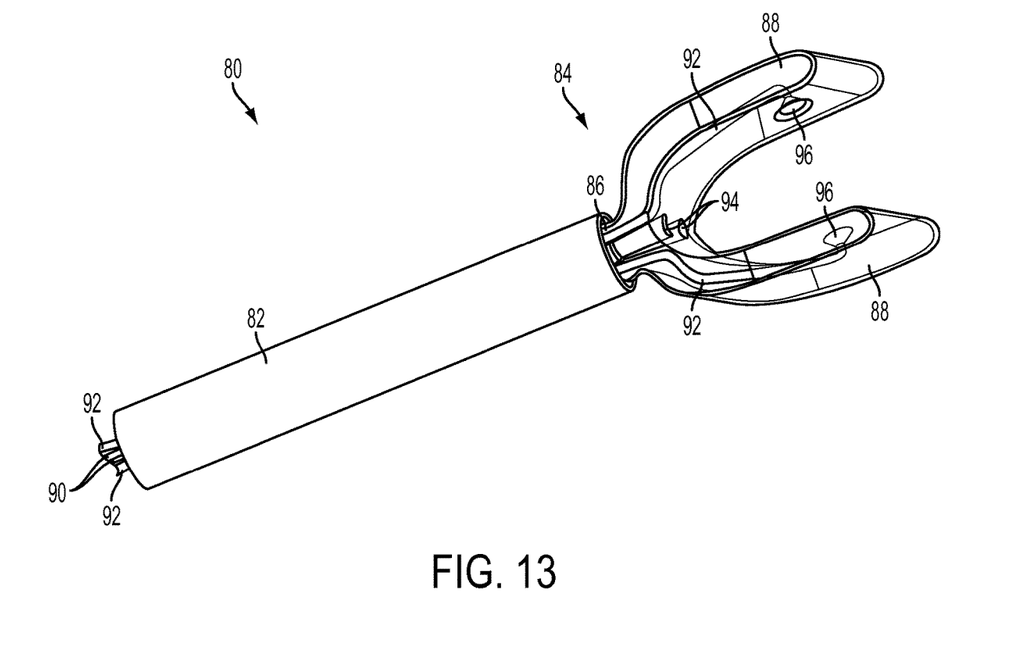
Figure 14:
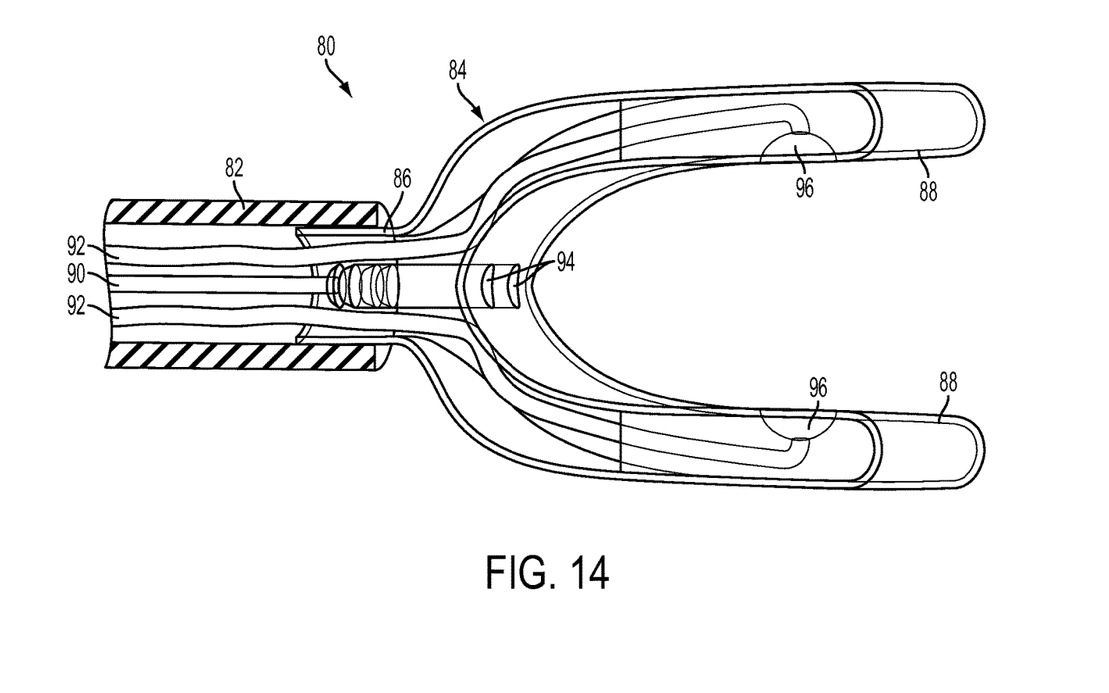
Figure 15:
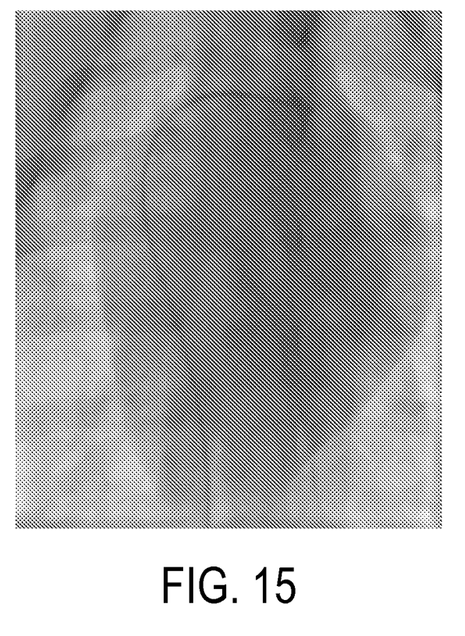
FIG. 15 shows an angiography of the right atrial appendage (RAA).
Figure 16:
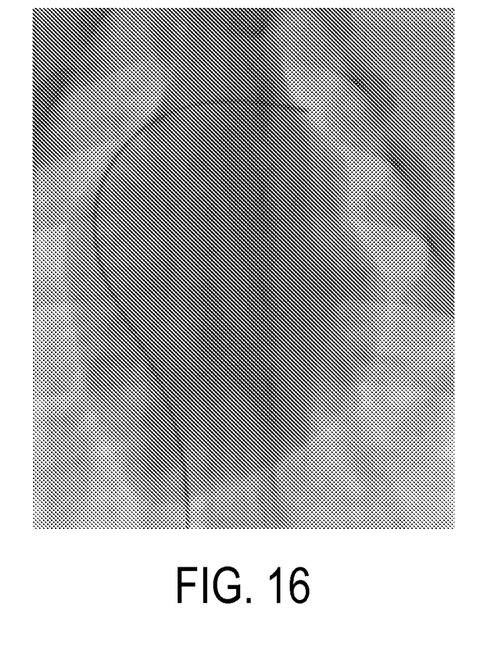
FIG. 16 illustrates puncture from the RAA into the pericardium.
Figure 17:
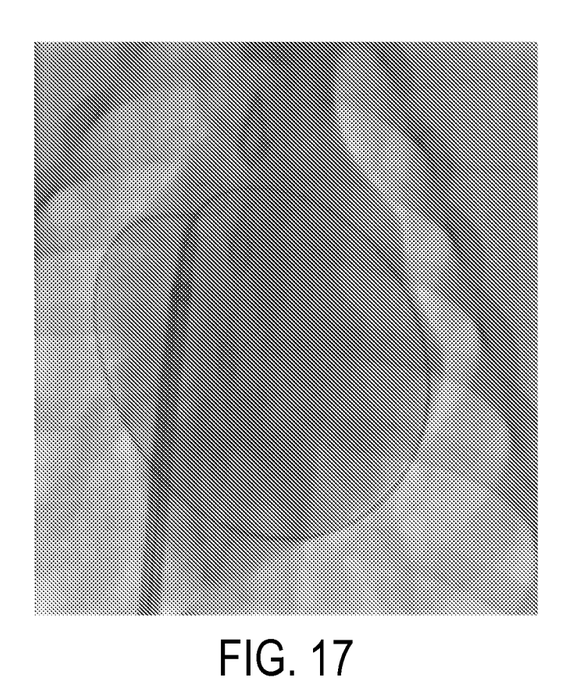
FIG. 17 shows introduction of the delivery limbs into the pericardium, and the resilient deformation of the limbs into a loop-shape. Iodinated contrast material is introduced into the pericardium in FIGS. 18 and 19. The left atrial appendage is grasped with a traction device in FIG. 20 to manipulate the LAA as in FIG. 21.
Figure 18:
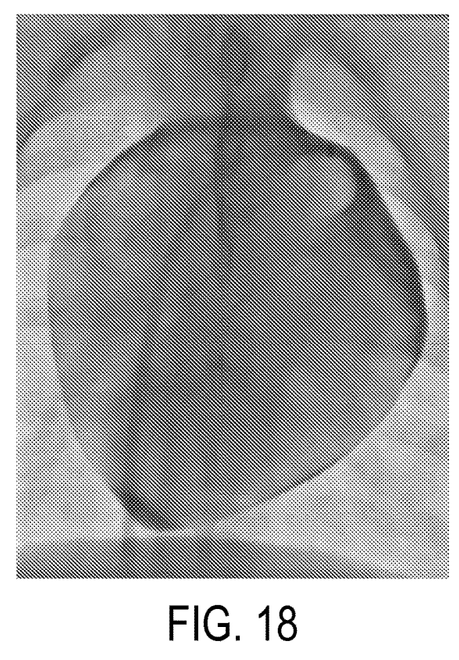
Figure 19:
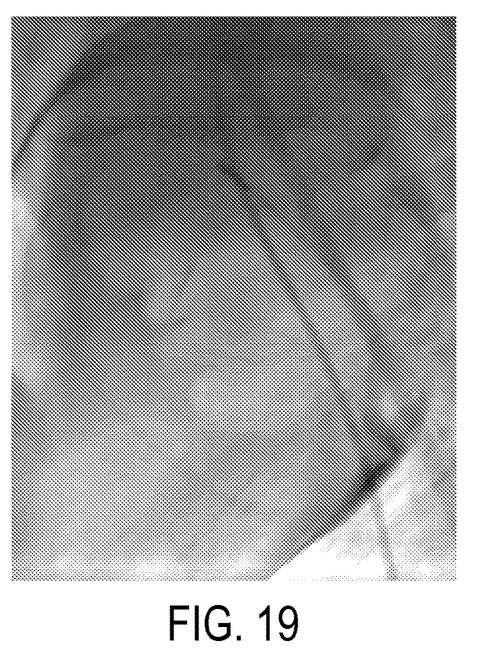
Figure 20:
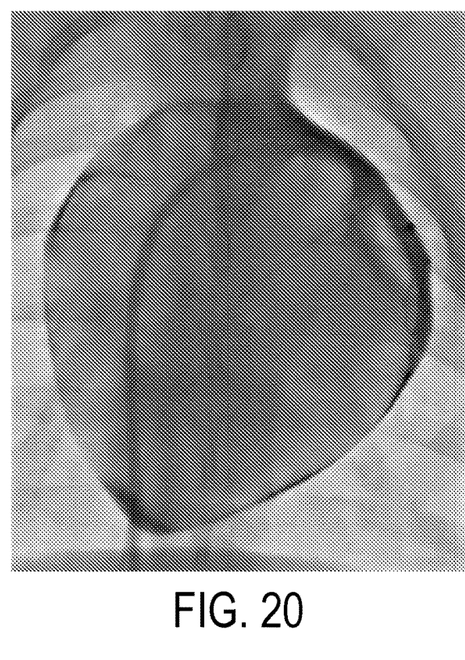
Figure 21:
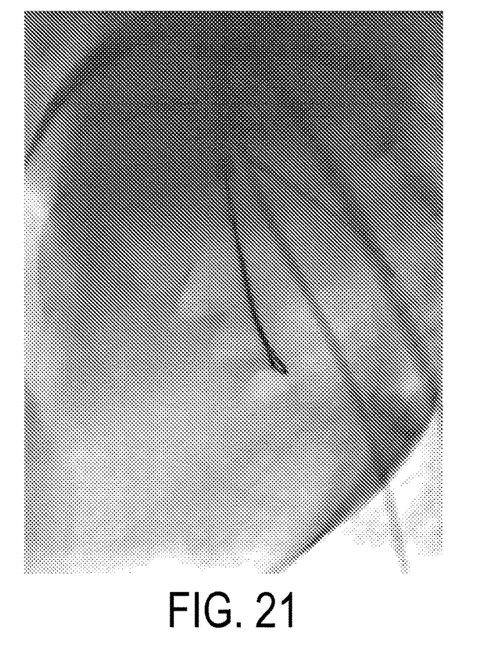

To adjust the size of the gap between the two wings 88, the vacuum tubes 90 and the catheter 82 can be moved axially relative to one another. For example, the vacuum tubes 90 can be pulled proximally relative to the catheter 82 to draw the suction ports 94 at the junction of the wings proximally relative to the distal end of the catheter, which causes the two wings 88 to articulate toward each other. As the suction ports 94 at the junction of the wings are pulled proximally, the distal end of the catheter 82 contacts the outer surfaces of the wings 88 and pushes the wings toward each other. The gripper 88 can have a natural configuration with the wings 88 spread at a maximum open angle, such that as the vacuum tubes 90 move (e.g., are pushed) distally relative to the catheter 82 and the force from the distal end of the catheter on the outer surfaces of the wings 88 is decreases, the wings can resiliently return toward the natural spread apart configuration (FIG. 11). After completion of a procedure, the entire gripper 84 may be drawn proximally into the catheter 82 in a resiliently compressed state.

The vacuum tubes 90 can include a reinforcement layer, such as a braiding layer, to increase their pushability, or column strength, so that they can be used to push and pull the gripper 84 to cause articulation of the wings 88. The vacuum tubes 92 can be softer and more flexible than the vacuum tubes 90, and can for example comprise a shape memory material to allows them to regain a predetermined shape and orientation within the wings 88 upon deployment from the catheter 82.

In various alternative embodiments, different combinations of the illustrated suction ports 94, 96 and/or other suction ports can be provided on the abluminal surface of the gripper 84. In some embodiments, the suction ports 94 are not present, and the tubes 90 can be used for articulating the wings 88 and not for providing suction, in which case the tubes 90 can instead comprise solid rods without a lumen. In some embodiments, additional suction ports can be provided on other regions of the abluminal inner surface of the gripper 84.

One benefit of using a suction-based traction device, such as the devices 50, 70, or 80, is that suction can allow the traction device to detach from the surface of the target structure before avulsion, tearing, or other unwanted damage occurs to the target structure. The suction-based traction device will detach once a sufficient tension is applied to overcome the suction force. The suction force at each of the suction ports or suction cups can be low enough that the traction device will detach from the target structure before avulsion occurs.

In some exemplary methods of using the disclosed suction based traction devices, the device can be delivered and applied from within the right atrial appendage via a transatrial approach. For example, the catheter can be directed transvascularly to the right atrium via the venous system and passed through the RAA into the pericardial space. In other exemplary methods of using the disclosed suction based traction devices, the device can be delivered and applied from a subxiphoid or transthoracic entry and intrapericardial or intravascular trajectory to the external surface of the LAA. For example, any of the disclosed devices may be inserted through a subxiphoid percutaneous entry and passed through the pericardium to access the LAA. Other delivery and application approaches can also be used. Regardless of the delivery and application approach used, the disclosed traction devices can be positioned alongside or coaxial with and used in an interactive manner with a therapy delivery system for applying a suture, clip, staple, etc. to occlude the LAA from outside of the LAA by an approach through the pericardial space.

Any of the disclosed devices can be used to ligate the RAA in a similar manner and using similar methods as re described for ligating the LAA.

In view of the many possible embodiments to which the principles of the disclosed technology may be applied, it should be recognized that illustrated embodiments are only examples and should not be considered a limitation on the scope of the disclosure. Rather, the scope of the disclosure is defined by the following claims. We therefore claim all that comes within the scope and spirit of these claims.

The invention claimed is:

1. A device for ligating the left atrial appendage, comprising:
    a delivery catheter configured to be directed into the pericardial space adjacent the left atrial appendage, the delivery catheter defining a longitudinal catheter axis that extends lengthwise along the delivery catheter;
    a traction device extending through the delivery catheter that non-traumatically grasps an outer surface of the left atrial appendage using suction and applies traction to the left atrial appendage, the traction device comprising a distal gripper that comprises an tubular neck positioned within the delivery catheter and two wings extending distally from the neck, wherein the two wings articulate open and closed about a gripper axis that is perpendicular to the longitudinal catheter axis, wherein the distal gripper comprises a resiliently deformable material that allows the two wings to resiliently flex relative to the neck to articulate open and closed, wherein the two wings each comprise an independent wing sucker that attaches to surfaces of the left atrial appendage using suction, wherein the distal gripper further comprises two intermediate suckers positioned between the two wings along the gripper axis that attach to surfaces of the left atrial appendage using suction, and wherein the wing suckers and the intermediate suckers are coupled to independent vacuum tubes that run from the respective sucker through the tubular neck and through the delivery catheter; and a delivery device that delivers a ligation device to the left atrial appendage while the traction is applied by the traction device.

2. The device of claim 1, wherein the delivery catheter is adapted to be delivered through the right atrial appendage into the pericardial space to adjacent the left atrial appendage.

3. The device of claim 1, wherein the traction device includes a resiliently deformable pad positioned around each of the suckers, the pads providing increased surface area for non-traumatically contacting surfaces of the left atrial appendage.

4. The device of claim 1, wherein each sucker is independently coupled to a vacuum source via discrete vacuum tubes that extend through the delivery catheter.

5. The device of claim 1, wherein each sucker is positioned at a distal end of an independent vacuum conduit extending through the delivery catheter, and the vacuum conduits comprise a shape memory material that resiliently regains a predetermined shape when released from a distal end of the delivery catheter.

6. The device of claim 1, wherein an articulation angle between the two wings is adjustable by relative axial motion between the delivery catheter and the two wings.

7. The device of claim 1, wherein the articulation angle between the two wings is adjustable by relative motion between the delivery catheter and a rod or vacuum tube positioned within the delivery catheter and coupled to a junction between the two wings.

8. The device of claim 1, wherein each of the two wings comprises a broad, deformable surface positioned around the suckers located in the wings, the deformable surfaces providing increased surface area for non-traumatically contacting surfaces of the left atrial appendage.

9. The device of claim 1, wherein the delivery device comprises a pre-shaped, articulated interrupted shape-memory loop that carries a suture.

10. The device of claim 1, wherein the delivery device comprises a hollow loop with a suture inside, or a solid loop inside a hollow suture, and the delivery device comprises separable segments that are withdrawn to leave only the suture in place around the left atrial appendage.

11. A method of left atrial appendage ligation comprising:
advancing a delivery catheter into a pericardial space, the delivery catheter defining a longitudinal catheter axis that extends lengthwise along the delivery catheter;

advancing a traction device from a distal end of the delivery catheter into the pericardial space such that a resiliently deformable distal portion of the traction device resiliently enlarges to an operative configuration when free of compression from the delivery catheter, the distal portion of the traction device comprising a gripper that comprises a neck and two wings extending from the neck, and wherein the two wings comprise two or more wing suckers and the gripper further comprises two or more intermediate suckers positioned at a junction between the wings, wherein the two wings articulate apart from each other about a gripper axis that is perpendicular to the longitudinal catheter axis to allow the traction device to enlarge to the operative configuration;

retracting the gripper relative to the delivery catheter such that the delivery catheter forces the two wings to articulate toward each other to grip the left atrial appendage;

securing the wing suckers and the intermediate suckers to a left atrial appendage using suction applied from a proximal control end of the delivery catheter via respective tubes that run through the neck to the suckers, and then manipulating the left atrial appendage via the traction device to facilitate placement of a ligation device on the left atrial appendage, or a neck or base thereof; and advancing a delivery device for the ligation device from the distal end of the delivery catheter and positioning the ligation device on the left atrial appendage, or a neck or base thereof.

12. The method of claim 11, further comprising;
detaching the traction device from the left atrial appendage and withdrawing the traction device proximally into the delivery catheter, and withdrawing the delivery device proximally into the delivery catheter while leaving the ligation device on the left atrial appendage, or neck or base thereof.

13. The method of claim 11, wherein the method comprises adjusting a distance between two of the suckers based on an anatomical size of the left atrial appendage prior to securing the suckers to the left atrial appendage.

14. The method of claim 12, wherein the suckers are secured to the left atrial appendage in a series.

15. The method of claim 12, wherein the method includes adjusting spacing between the wings by pulling or pushing a tube or rod attached to a junction between the two wings.

16. The method of claim 12, wherein the method comprises advancing the delivery catheter into the pericardial space from within the right atrial appendage.

17. The method of claim 12, wherein the method comprises advancing the delivery catheter into the pericardial space through the pericardium.

18. The method of claim 12, wherein the method comprises delivering the delivery catheter into the pericardial space from a subxiphoid transpericardial approach.

* * * * *